United States Patent
Wiley et al.

(10) Patent No.: US 11,045,086 B2
(45) Date of Patent: Jun. 29, 2021

(54) DEVICE AND METHOD FOR MARKING THE CORNEA

(71) Applicants: William F. Wiley, Chagrin Falls, OH (US); John P. Berdahl, Sioux Falls, SD (US)

(72) Inventors: William F. Wiley, Chagrin Falls, OH (US); John P. Berdahl, Sioux Falls, SD (US)

(*) Notice: Subject to any disclaimer, the term of this patent is extended or adjusted under 35 U.S.C. 154(b) by 552 days.

(21) Appl. No.: 15/343,913

(22) Filed: Nov. 4, 2016

(65) Prior Publication Data
US 2017/0127939 A1 May 11, 2017

Related U.S. Application Data

(60) Provisional application No. 62/252,023, filed on Nov. 6, 2015.

(51) Int. Cl.
| | |
|---|---|
| *A61B 3/107* | (2006.01) |
| *A61F 9/013* | (2006.01) |
| *B41F 17/00* | (2006.01) |
| *A61B 3/135* | (2006.01) |
| *A61B 3/16* | (2006.01) |
| *A61F 9/007* | (2006.01) |
| *B41F 17/30* | (2006.01) |
| *B41M 1/26* | (2006.01) |
| *B41M 1/40* | (2006.01) |

(52) U.S. Cl.
CPC .............. *A61B 3/107* (2013.01); *A61B 3/135* (2013.01); *A61B 3/16* (2013.01); *A61F 9/007* (2013.01); *A61F 9/0136* (2013.01); *B41F 17/006* (2013.01); *B41F 17/30* (2013.01); *B41M 1/26* (2013.01); *B41M 1/40* (2013.01)

(58) Field of Classification Search
None
See application file for complete search history.

(56) References Cited

U.S. PATENT DOCUMENTS

| | | | |
|---|---|---|---|
| 4,875,767 A * | 10/1989 | Wright | ..................... A61B 3/15 351/212 |
| 5,013,319 A | 5/1991 | Davis | |
| 5,245,367 A | 9/1993 | Miller et al. | |

(Continued)

OTHER PUBLICATIONS

Arlt, EM et al., "Implantable inlay devices for presbyopia: the evidence to date," Clin Ophthalmol. 2015; 9: 129-137 (Published online Jan. 14, 2015), https://www.ncbi.nlm.nih.gov/pmc/articles/PMC4298303/. (Year: 2015).*

(Continued)

*Primary Examiner* — Matthew Kremer
(74) *Attorney, Agent, or Firm* — Patterson Thuente Pedersen, P.A.

(57) ABSTRACT

A device and method for marking corneal tissue is disclosed. The device includes an ink reservoir portion and an ink resist portion. The ink reservoir portion is annular in shape and the ink resist portion occupies a central area within the annular shape. The ink reservoir portion and the ink resist portion are sized and structured to interface with the central cornea and to apply ink to the corneal tissue. The method includes applying ink to the cornea in an annular pattern.

8 Claims, 11 Drawing Sheets

(56) References Cited

U.S. PATENT DOCUMENTS

| | | | |
|---|---|---|---|
| 5,578,049 A * | 11/1996 | Feaster | A61F 9/0136 |
| | | | 606/166 |
| 6,283,595 B1 | 9/2001 | Breger | |
| 7,976,577 B2 | 7/2011 | Silvestrini | |
| 2005/0033420 A1 * | 2/2005 | Christie | A61F 2/147 |
| | | | 623/5.12 |
| 2005/0046794 A1 | 3/2005 | Silvestrini et al. | |
| 2005/0203554 A1 | 9/2005 | Dykes | |
| 2005/0245948 A1 | 11/2005 | Khalaj | |
| 2006/0265058 A1 * | 11/2006 | Silvestrini | A61F 2/14 |
| | | | 351/159.63 |
| 2012/0203239 A1 * | 8/2012 | Vukich | A61B 3/152 |
| | | | 606/107 |
| 2013/0035705 A1 | 2/2013 | Fath et al. | |
| 2014/0107631 A1 | 4/2014 | Ferrari | |
| 2015/0150723 A1 * | 6/2015 | Brown | A61F 9/0136 |
| | | | 606/166 |
| 2015/0305927 A1 * | 10/2015 | Walter | A61F 9/0008 |
| | | | 606/5 |

OTHER PUBLICATIONS

Mandel, Mark, "Kamra Inlay for Presbyopia," https://optimaeye.com/kamra-inlay-for-presbyopia/ (This entry was posted in Eye Health, Presbyopia Correction on Aug. 14, 2015). (Year: 2015).*

Tomás-Juan, Javier, "Small aperture corneal inlay for the correction of presbyopia: visual results and complications," Journal of Emmetropia, vol. 5, Apr.-Jun. 2014, pp. 99-103. (Year: 2014).*

International Preliminary Report on Patentability (IPRP) for International Application No. PCT/US2016/060773, dated May 8, 2018, 8 pages.

International Search Report and Written Opinion for International Application No. PCT/US2016/060773, dated Mar. 6, 2017.

* cited by examiner

DEVICE AND METHOD FOR MARKING THE CORNEA

CLAIM TO PRIORITY

This application claims the benefit of U.S. Provisional Patent Application 62/252,023 filed Nov. 6, 2015 and entitled Device and Method for Marking the Cornea, the entire contents of which are incorporated herein by reference.

FIELD OF THE INVENTION

The invention relates to corneal marking and the application of ink to the corneal surface were within the cornea. The invention further relates to a method of predicting the likelihood of success with a corneal inlay of a pinhole type.

BACKGROUND OF THE INVENTION

Presbyopia is a condition of the eyes that arises with age. The flexibility of the eye's natural focusing system declines with time. Eventually the eye is less able to focus from distance to near to see near objects clearly. The gradual occurrence of the loss of ability to focus on near objects until reading becomes difficult is identified as presbyopia. It is generally understood that presbyopia occurs because the natural crystalline lens inside the eye gradually loses flexibility over time and is less resiliently responsive to reduced tension of the lens zonules that occurs because of contraction of the annularly shaped ciliary muscle in the ciliary body. Presbyopia is commonly compensated for by the use of multi-focal eyeglasses, contact lenses, reading glasses or other visual aids to provide additional assistance in focusing on near objects.

Recently, another approach to treating presbyopia has developed involving the application of corneal inlays. Corneal inlays are intended to prove near vision, ideally without compromising distance vision, in emmetropic presbyopia and possibly in presbyopic patients who also have other refractive errors. Three variations on the corneal inlay concept are known to either be available or in development at the time this application. A corneal inlay is placed within the cornea, generally in the anterior half of the cornea, through a small incision in the cornea or by creation of a corneal flap. When implanted, the structure of the corneal inlay lies generally parallel to the anterior surface of the cornea.

Three different corneal inlay approaches are available. A first approach attempts to create multi-focal vision by using an in-cornea lens that is implanted as a corneal inlay. A second approach attempts to make the cornea multi-focal by reshaping it by placement of the inlay within the cornea. Lastly, the Kamra® inlay from Accufocus in Irvine, Calif. uses the pinhole principal to increase depth of field and to provide assistance for near focusing.

Of particular interest for this application is the Kamra® corneal inlay which works on the basis of the pinhole effect. The pinhole effect increases depth of field by restricting the diameter of pencils of light entering the eye. The pinhole effect is known to many photographers who are aware that they can increase depth of field in photographs by using a small lens aperture when the photograph is taken. The same effect is utilized in a pinhole camera. Because of the pinhole effect light is limited to passing only through the center or a small portion of the lens of the eye, a pinhole aperture thus minimizes the effect of refractive error upon focusing by narrowing the diameter of pencils of light entering the eye and minimizes the size of blur circles presented on the retina.

Pinhole contact lenses which attempt to take advantage of the pinhole effect to improve focusing in presbyopia and other refractive errors have been known for many years. The use of the pinhole effect in the Kamra® corneal inlay is somewhat different from a pinhole contact lens in that the inlay includes a dark annulus surrounding a small aperture of approximately 1.6 mm diameter. In addition, the Kamra® corneal inlay is reported to include a very large number of very small 5 to 11 µm holes in the annular dark portion.

The surgical procedures utilized to implant corneal inlays have been demonstrated, so far, to be quite safe. Nonetheless placement of a corneal inlay within the corneal tissue is a surgical procedure and is significantly invasive and incurs the risks normally involved in any surgical procedure of the cornea.

Further, many patients are excluded from a surgical procedure to implant a corneal inlay by some preexisting factor in their health history. Particularly, patients may be excluded if they have had previous ocular surgeries or if they have any ocular pathology including corneal ectasia, corneal degeneration, severe blepharitis, retinal disease, glaucoma, cataract, significant corneal topographic irregularities or severe dry eye.

Corneal inlays have other disadvantages. Generally, these corneal inlays reduce distance vision to some degree while providing a benefit for near vision. While that tradeoff for improving reading vision is acceptable to some patients, it is unacceptable to others. Corneal inlays have also been demonstrated to cause glare in night vision to some degree, which is a consequence of changing the way the eye focuses light. Accordingly, if patients utilizing a corneal inlay are unhappy, it is often because their night vision is not good enough or their distance vision is not good enough or their reading vision is not sufficiently helpful.

Accordingly, the inlays can be explanted. Corneal inlays can be surgically removed if the patient is unhappy with the results. Reasons for dissatisfaction may include insufficient visual improvement, reduced distance vision or other visual compromise. Vision usually returns to being very close to what it was before surgery but may not be equal to vision prior to the procedures. Many patients are reluctant to undergo a surgical procedure to test whether they will find the visual effect of the corneal inlay acceptable. If the corneal inlay does not provide a comfortable visual situation for them they are reluctant to have a second surgical procedure to remove the corneal inlay.

There is presently no procedure known to the inventors to simulate the effect of a corneal inlay without actual implantation of the corneal inlay. Accordingly, there is still room for improvement in the ophthalmological arts as to predicting the likelihood of success with a corneal inlay of the pinhole type.

SUMMARY OF THE INVENTION

Embodiments of the invention solve many of the above discussed problems by providing for the application of surgical ink to the corneal surface or corneal tissue to simulate the effect of a corneal inlay of the pinhole type. Accordingly, the embodiments of the invention include a method of application of ink to the corneal surface to simulate the effect of a pinhole corneal inlay. Embodiments of the invention also include a method of applying surgical ink to the corneal surface or to an autologous corneal graft that can be inlaid in the cornea.

Further embodiments of the invention includes device for the application of ink to the corneal surface to simulate the effect of a pinhole corneal inlay. A variety of different embodiments of the invention include different approaches.

According to an example embodiment of the invention, an inking device probe that replaces the probe on a Goldman tonometer is provided to apply ink to the anterior corneal surface. The inking device probe includes an ink reservoir portion and an ink resist portion. The ink reservoir portion may be annular in structure while the ink resist portion is located in the central circular aperture of the annulus.

According to another example embodiment of the invention, a device somewhat similar to a Goldman tonometer is provided to apply ink to the anterior corneal surface. Here again, the device includes an ink reservoir portion and an ink resist portion, the ink reservoir portion annularly surrounding the ink resist portion. The device is mountable on a slit lamp biomicroscope so that the biomicroscope can be used to guide the application of ink to the cornea.

Accordingly to another embodiment of the invention, a well device is used to apply surgical ink to the anterior corneal surface while the patient is supine and the eye is looking vertically upward. This is commonly the posture of the patient when positioned at a surgical microscope. The well device includes an annular ink reservoir and centrally located ink resist portion that apply ink to the cornea to simulate the effect of a pinhole type corneal inlay.

According to another embodiment of the invention, a hand held ink application device is provided. The hand held ink application device may include an ink reservoir including a sponge or rubber stamp portion. The hand held ink application device can be used freehand, with a slit lamp or used along with a surgical microscope for eye surgery. Further embodiments of the hand-held ink application device can provide for self administration of surgical ink to the corneal surface utilized with a mirror. Further, according to another example embodiment of the invention, a handheld sponge type device is configured to self-administer ink to the cornea with the assistance of a camera or cell phone attachment.

According to another example embodiment of the invention, a surgical ink application of the cornea is utilized for long term treatment of presbyopia by utilizing a permanent ink. Permanent in this context is relative. The corneal epithelium is a cellular structure the cells of which are replaced at a very rapid rate. Accordingly, ink applied to the corneal epithelial surface is rapidly lost due to cell replacement. Thus, ink may be applied deep to the corneal surface for longer term treatment in the manner of a corneal tattoo.

According to another example embodiment of the invention, Inc. is applied to an autologous tissue that is then inserted into the cornea through a pocket or under a corneal flap. In this case a corneal lenticle can be removed from the eye for example in a procedure similar to the SMILE technique. According to this embodiment of the invention, the removed corneal lenticle could have ink applied to it as discussed herein and at the time of surgery or at some future time when the patient develops presbyopia the lenticle can be reinserted into the eye.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Figure 1:
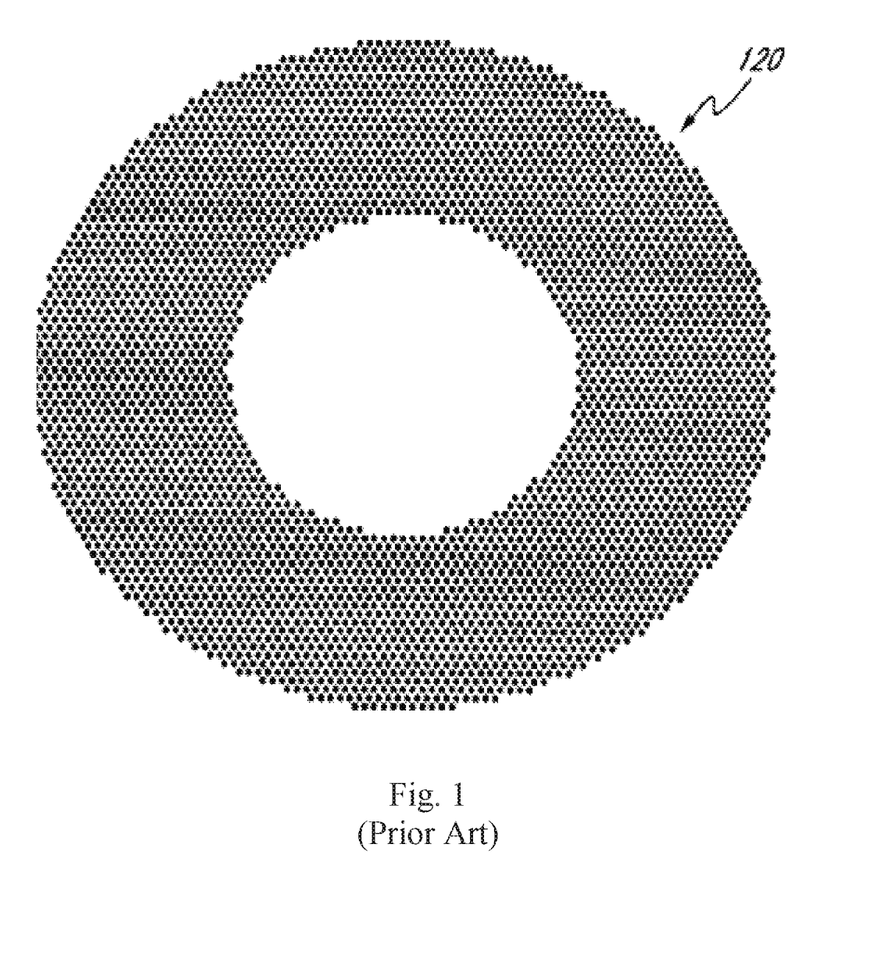
FIG. 1 is a front elevational view of a pinhole type corneal inlay according to the prior art.

Referring to FIG. 1, a prior art pinhole type corneal inlay 20 is depicted. Pinhole type corneal inlay 20 includes annular disk 22, and central circular aperture 24. Pinhole type corneal inlay 20 also presents multiple microapertures 26 in annular disk 22. Microapertures 26 are understood to be transparent spaces in annular disk 22.

Figure 2:
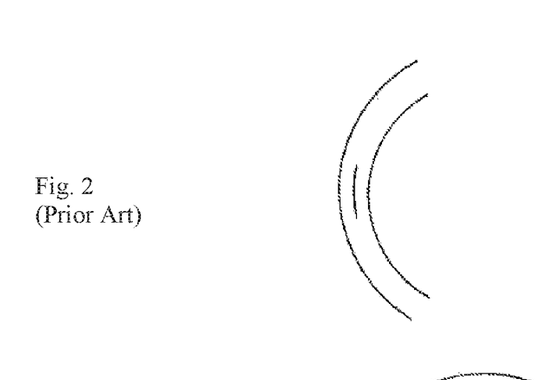
FIG. 2 is a side sectional view of a pinhole type corneal inlay implanted in a cornea according to the prior art.

Referring to FIG. 2, pinhole type corneal inlay 20 is depicted as implanted in cornea 28. It is noted that this is a schematic depiction and the layers of the cornea as well as the specific depth of implantation are not necessarily depicted in FIG. 2.

Figure 3:
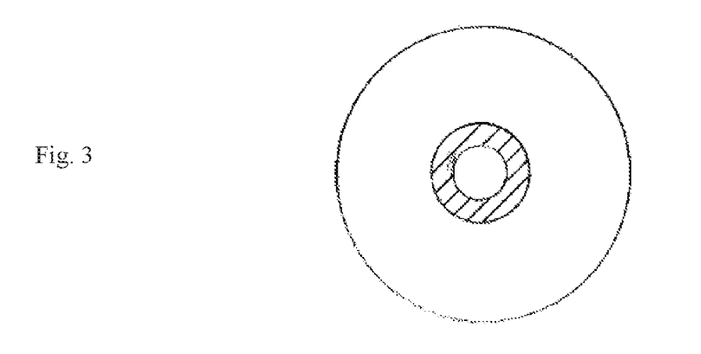
FIG. 3 is a front view of a cornea with an application of surgical ink to simulate the effect of a corneal inlay of the pinhole type.

Referring now to FIG. 3, annular inked area 30 surrounding central circular aperture 32 is depicted.

Figure 4:
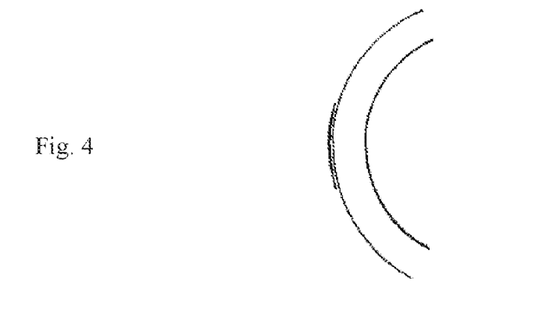
FIG. 4 is a side sectional view of a cornea with ink applied to the anterior corneal epithelium according to an example embodiment of the invention.

Referring also to FIG. 4, it is notable that annular inked area 30 according to the present invention is located on the corneal epithelial surface 34. Annular inked area 30 is created by the application of surgical ink applied to corneal epithelial surface 34 according to embodiments of the invention.

Figure 5:
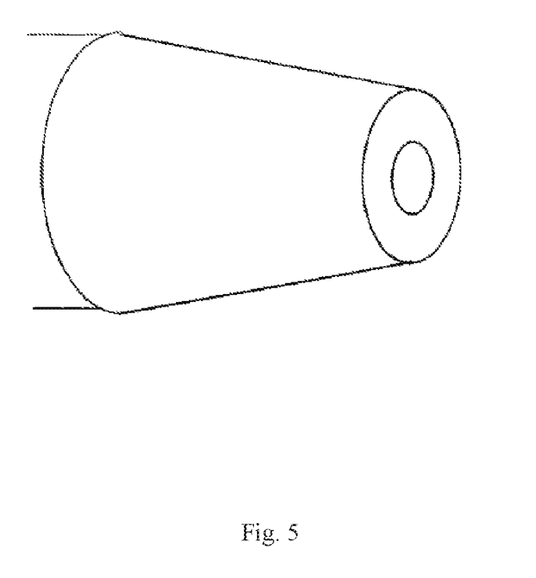
FIG. 5 is a front perspective view of a corneal ink applicator according to an example embodiment of the invention.

Referring now to FIG. 5, corneal ink applicator 36, according to an example embodiment of the invention, is depicted. Corneal ink applicator 36 generally includes applicator body 38 having applicator tip 40. Applicator tip 40 generally presents ink reservoir portion 42 and ink resist portion 44. In the depicted embodiment, applicator body 38 further includes tonometer coupling portion 46 including coupling barrel 48. Coupling barrel 48 is sized to match a similar portion of a Goldmann tonometer prism in order that applicator 38 may be placed in a Goldmann tonometer which is commonly available in the offices of eye doctors and used for measuring intraocular pressure.

Ink reservoir portion 42 is formed of a material adapted to absorb and release ink. For example, ink reservoir portion may include a porous, rubber or foam material as well as a ground glass surface.

Figure 6:
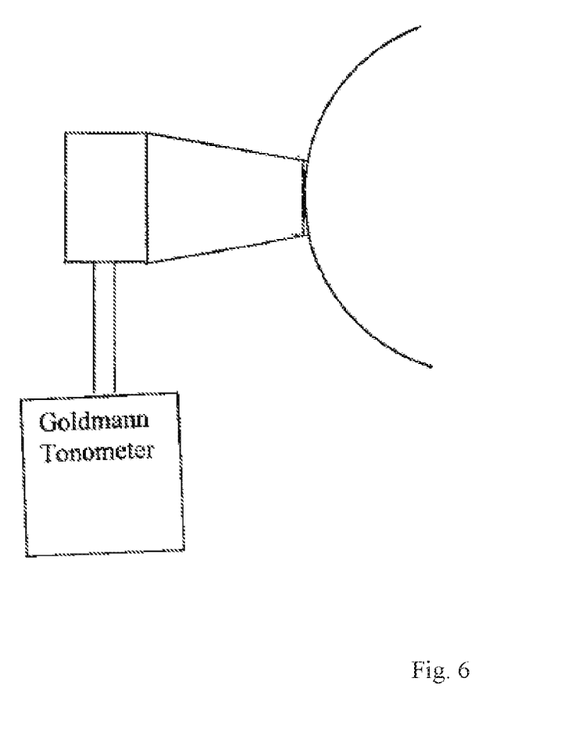
FIG. 6 is a side elevational view corneal ink applicator adapted to be used with a Goldmann tonometer according to an example embodiment of the invention.

Ink resist portion 44 is glossy and smooth and formed of a material that resists the absorption and release of ink. Ink resist portion 44 may also include a cavity or space. Referring to FIG. 6, corneal ink applicator 36 is schematically depicted as coupled to a Goldmann tonometer 50 and in contact with schematically depicted cornea 28.

According to an example embodiment, ink reservoir portion 42 has an outside diameter between about 3.2 and 4.4 mm. According to a further example embodiment, ink reservoir portion 42 has an outside diameter of approximately 3.6 mm. According to another example embodiment, ink resist portion 44, located centrally in ink reservoir portion 42, has a diameter between about 1.0 and 2.2 mm. According to a further example embodiment, ink resist portion 44 has a diameter of 1.8 mm.

Figure 7:
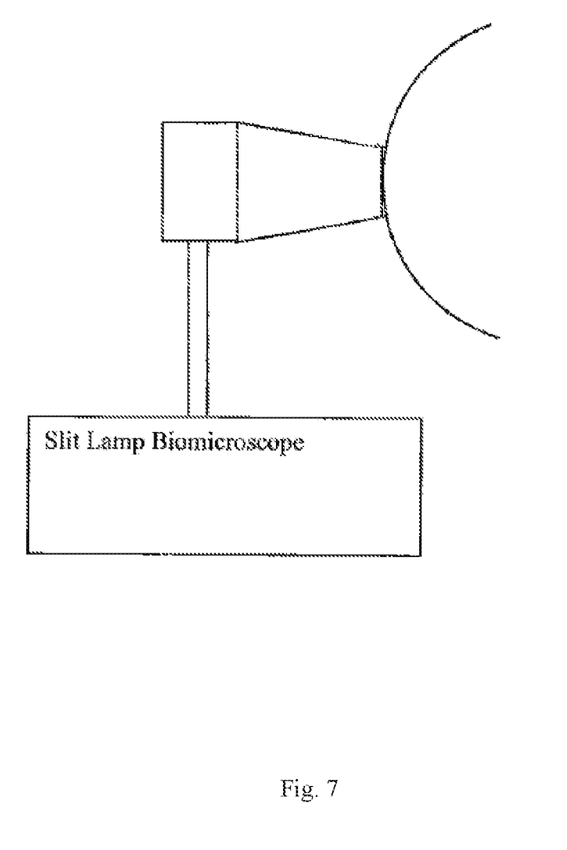
FIG. 7 is a side elevational view corneal ink applicator adapted to be used with a slit lamp biomicroscope according to an example embodiment of the invention.

Referring now to FIG. 7, another example embodiment of corneal ink applicator 36 is depicted. In the depicted embodiment, corneal ink applicator 36 includes slit lamp coupling portion 52. Slit lamp coupling portion 52 generally includes corneal applicator holding member 54 and slit lamp engaging member 56 which are adapted to couple corneal ink applicator 36 to slit lamp biomicroscope 58. Slit lamp engaging member 56 may be coupled to slit lamp biomicroscope 58 in a number of ways including ways similar to which a Goldmann tonometer is coupled to slit lamp biomicroscope 58. Slit lamp engaging member 56 may engage a microscope head (not shown) of slit lamp biomicroscope 58 or may engage slit lamp biomicroscope 58 at or near the slit lamp vertical rotational axis in a similar fashion to a focusing rod commonly used with slit lamp microscope 58.

Figure 8:
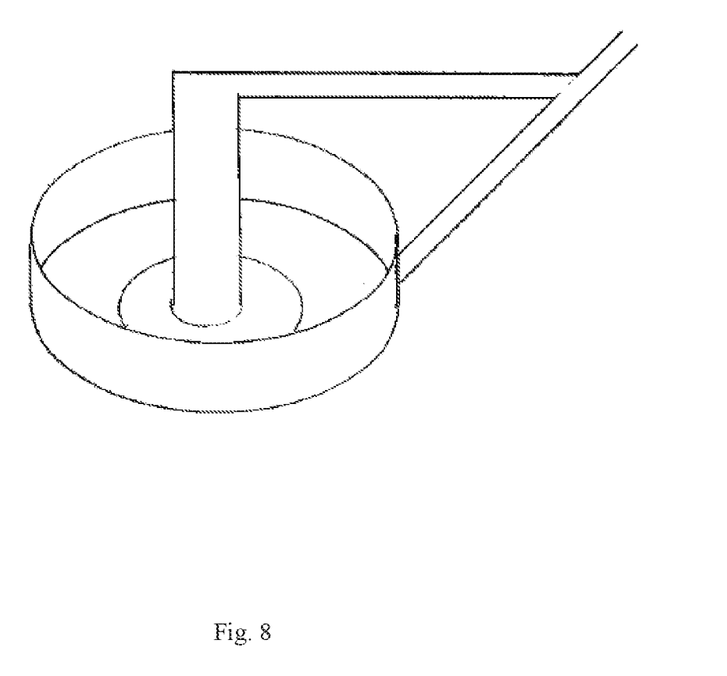
FIG. 8 is a perspective view of a well corneal ink applicator according to an example embodiment of the invention.

Referring to FIG. 8, well corneal ink applicator 60 according to another example embodiment of the invention is depicted.

In the depicted example embodiment, well corneal ink applicator 60 generally includes peripheral ring portion 62, central ink resist portion 64, ink resist support 66, ring support 68, and well handle 70. Peripheral ring portion 62 is coupled to ring support 68 which is in turn coupled to well handle 70. Central ink resist portion 64 is coupled to ink resist support 66 which is in turn coupled to well handle 70. Central ink resist portion 64 is separated from peripheral ring portion 62 by intervening space 72. Intervening space 72 is generally annular in shape. In the depicted embodiment, central ink resist portion 64 is generally circular in shape and centrally located within peripheral ring portion 62. Peripheral ring portion 62 may be formed of a biocompatible material such as surgical stainless steel, nitinol or a polymer material. Central ink resist portion 64 may be formed of a similar biocompatible material. Central ink resist portion 64 further includes ink resist disk 74 coupled to ink resist support 66. Ink resist disk 74 may be surfaced with a hydrophobic material such as a fluoropolymer for example Teflon®. Ink resist disk 74 may further include sealing rim 76. Peripheral ring portion 62 includes sealing edge 78 at a lower edge thereof.

Figure 9:
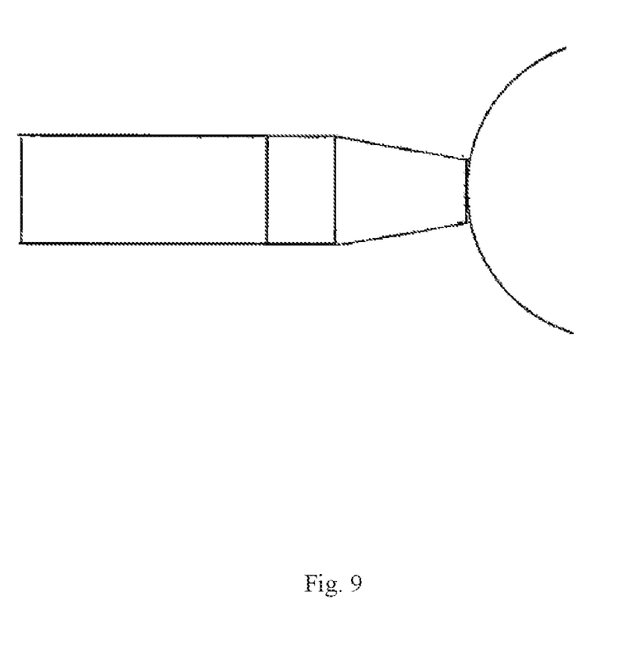
FIG. 9 is a schematic side view of a hand held corneal ink applicator according to an example embodiment of the invention.

Referring now to FIG. 9, hand held ink application device 80 is depicted. Hand held ink application device 80 includes a structure similar to corneal ink applicator 36 as well as holder portion 82. Corneal ink applicator 36 is coupled to holder portion 82 so that holder portion 82 may be held in the hand of an eye care professional making the ink application. Holder portion 82 or corneal ink applicator 36 may also include a fixation target 84 visible to the patient to assist in application.

Figure 10:
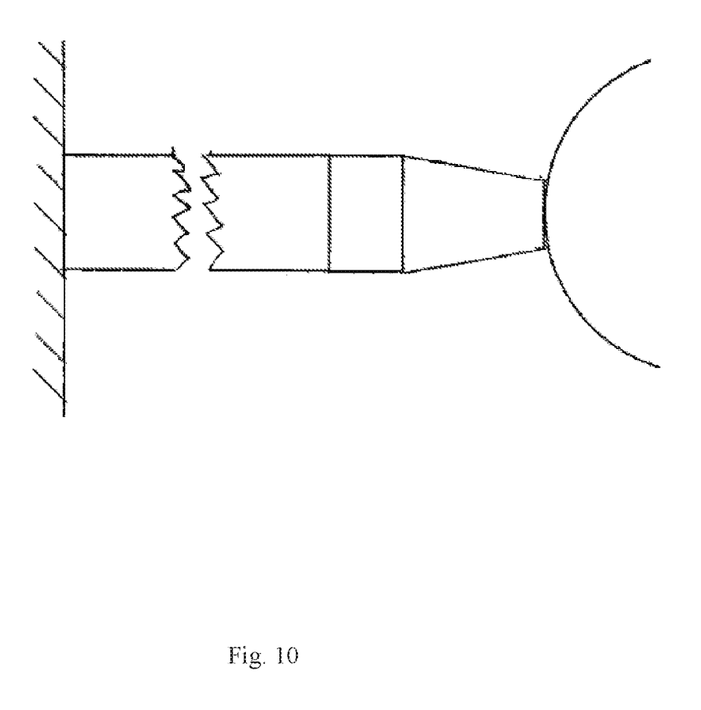
FIG. 10 is a schematic side view of a hand held corneal ink applicator including a mirror to facilitate self application according to an example embodiment of the invention.

Referring now to FIG. 10, hand held ink application device 80 may further include mirror 86 coupled thereto. Mirror 86 facilitates self application of corneal inking. Mirror 86 is depicted as a plano mirror. However, mirror 86 may also include a concave mirror to assist in visualizing the application process with magnification.

Figure 11:
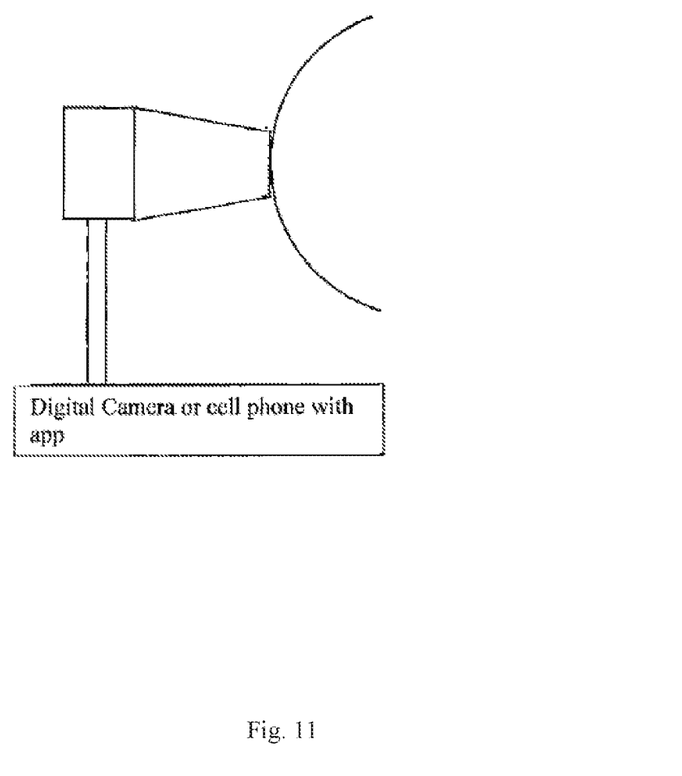
FIG. 11 is a schematic side view of a hand held corneal ink applicator including a camera or cell phone camera to facilitate self application according to an example embodiment of the invention.

Referring now to FIG. 11, hand held ink application device 80 may also include cell phone or camera coupler 88. Cell phone or camera coupler 88 is adapted to provide physical connection 90 and data connection 92 to digital camera or cell phone 94. Digital camera or cell phone 94 is thus physically and data connected to cell phone or camera coupler 88 in such a way to provide an image for self application of surgical ink to corneal epithelial surface 34.

Figure 12:
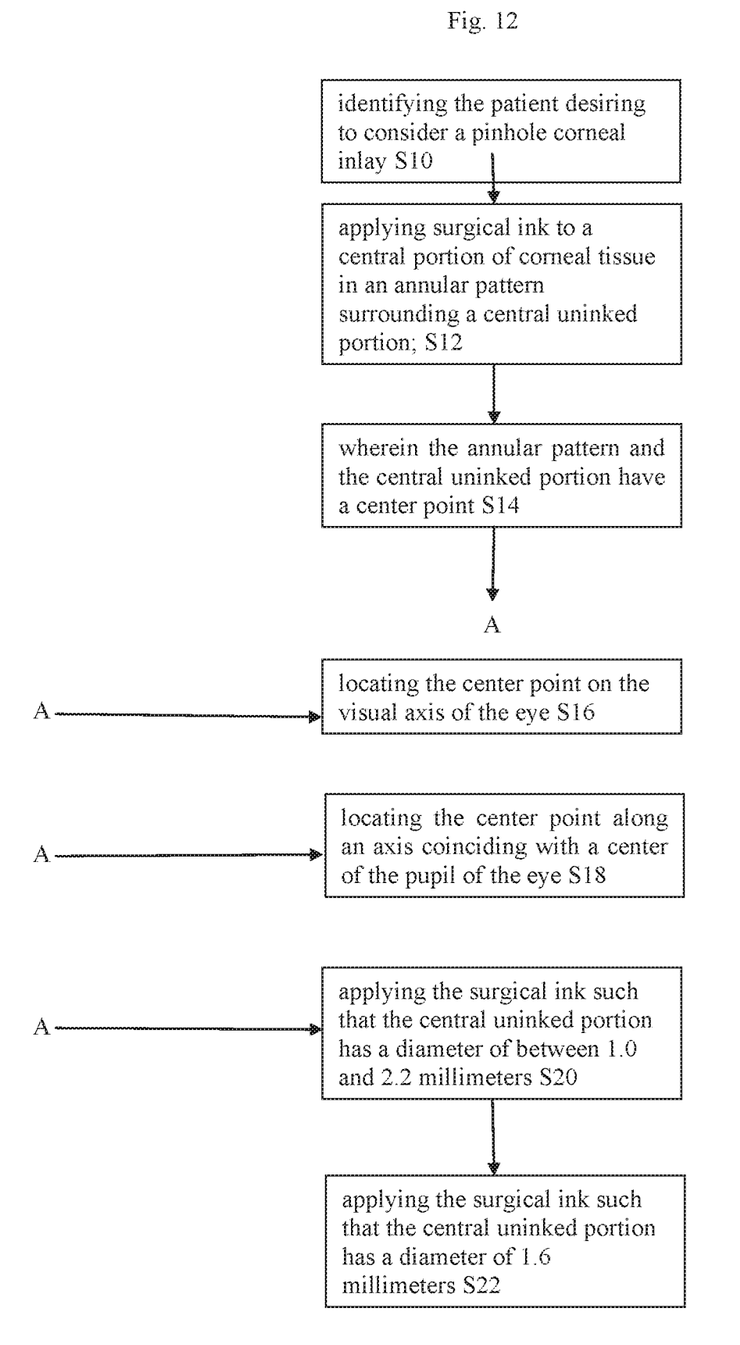
FIG. 12 is a flow chart depicting a method according to an example embodiment of the invention.

Referring now to FIG. 12, a method according to another example embodiment of the invention is depicted.

The example method includes identifying a patient desiring to consider a pinhole corneal inlay S10; applying surgical ink to a central portion of the corneal epithelium of the patient in an annular pattern surrounding a central uninked portion letter S12; wherein the annular pattern and the central uninked portion have a center point S14.

According to another example embodiment of the invention, the method includes locating the center point on the visual axis of the eye S16.

According to another example embodiment, the method includes locating the center point along an axis coinciding with a center of the pupil of the eye S18.

According to another example embodiment, the method includes applying the surgical ink such that the central uninked portion has a diameter of between 1.0 and 2.2 mm S20.

According to a further example embodiment, the method includes applying the surgical ink such that the central unlinked portion has a diameter of 1.6 mm S22.

According to a further example embodiment, the method includes applying the surgical ink such that the annular pattern has an outside diameter of between 3.2 and 4.4 mm S24. According to a further example embodiment, the method includes applying the surgical ink such that the annular pattern has an outside diameter of 3.6 mm S26.

According to yet another example embodiment, the method includes applying the surgical ink to an anterior surface of the corneal epithelium S28.

According to a further example embodiment, the method includes applying the surgical ink to a lenticle that has been surgically removed from the cornea S30. According to this embodiment, the surgical lenticle may be further reinserted into the cornea S32. Further according to this embodiment, the surgical lenticle may be stored for a period of time and reinserted into the cornea later S34.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. A method for evaluating a patient's likelihood of success with an implantable pinhole corneal inlay of an eye, comprising:
    identifying the patient considering the implantable pinhole corneal inlay;
    applying surgical ink to a central portion of a cornea not deeper than a corneal epithelium of the patient in an annular pattern surrounding a central uninked portion thereby temporarily simulating an optical effect of the implantable pinhole corneal inlay without implanting the corneal inlay until the surgical ink applied to the central portion of the corneal epithelium is lost due to cell replacement;
    wherein the annular pattern and the central uninked portion have a center point; and
    further comprising evaluating the patient's response to the simulated optical effect of the implantable pinhole corneal inlay achieved by the application of the surgical ink.

2. The method as claimed in claim 1, further comprising locating the center point on a visual axis of the eye.

3. The method as claimed in claim 1, further comprising locating the center point proximate an axis coinciding with a center of the pupil of the eye.

4. The method as claimed in claim 1, further comprising applying the surgical ink such that the central uninked portion has a diameter of between 1.0 and 2.2 millimeters.

5. The method as claimed in claim 1, further comprising applying the surgical ink such that the central uninked portion has a diameter of 1.6 millimeters.

6. The method as claimed in claim 1, further comprising applying the surgical ink such that the annular pattern has an outside diameter of between 3.2 and 4.4 millimeters.

7. The method as claimed in claim 1, further comprising applying the surgical ink such that the annular pattern has an outside diameter of 3.6 millimeters.

8. The method as claimed in claim 1, further comprising applying the surgical ink to an anterior surface of the corneal epithelium.

* * * * *